US012533294B2

(12) United States Patent
Demizu et al.

(10) Patent No.: US 12,533,294 B2
(45) Date of Patent: Jan. 27, 2026

(54) INFUSION CARTRIDGE AND INFUSION PUMP

(71) Applicant: TERUMO KABUSHIKI KAISHA, Tokyo (JP)

(72) Inventors: Shun Demizu, Hadano (JP); Shohei Sasaki, Chigasaki (JP)

(73) Assignee: TERUMO KABUSHIKI KAISHA, Tokyo (JP)

( * ) Notice: Subject to any disclaimer, the term of this patent is extended or adjusted under 35 U.S.C. 154(b) by 861 days.

(21) Appl. No.: 17/752,493

(22) Filed: May 24, 2022

(65) Prior Publication Data

US 2022/0287912 A1 Sep. 15, 2022

Related U.S. Application Data

(63) Continuation of application No. PCT/JP2020/039253, filed on Oct. 19, 2020.

(30) Foreign Application Priority Data

Nov. 28, 2019 (JP) ................................ 2019-215766

(51) Int. Cl.
*A61J 1/05* (2006.01)
*A61J 1/16* (2023.01)
(Continued)

(52) U.S. Cl.
CPC . *A61J 1/05* (2013.01); *A61J 1/16* (2013.01); *A61J 1/2075* (2015.05); *A61J 1/2082* (2015.05);
(Continued)

(58) Field of Classification Search
CPC .............. A61M 5/142; A61M 5/14228; A61M 5/14244; A61M 5/1413; A61M 2209/045;
(Continued)

(56) References Cited

U.S. PATENT DOCUMENTS 5,167,631 A * 12/1992 Thompson ............ A61M 5/152 222/386.5
5,492,533 A * 2/1996 Kriesel ............... A61M 5/1409 604/890.1
(Continued)

FOREIGN PATENT DOCUMENTS

CN 109925570 A 6/2019
JP S52-120593 A 10/1977
(Continued)

OTHER PUBLICATIONS

International Searching Authority, "International Search Report," issued in connection with International Patent Application No. PCT/JP2020/039253, dated Jan. 12, 2021.
(Continued)

*Primary Examiner* — Wesley G Harris
(74) *Attorney, Agent, or Firm* — Foley & Lardner LLP

(57) ABSTRACT

An infusion cartridge includes: a case portion having a portion that defines a recess; and a film portion that has flexibility and covers an open side of the recess. The film portion and said portion of the case portion together form an inner wall that defines a storage space configured to store an infusion solution. The infusion cartridge further includes: a filling port located at the inner wall and configured to allow the infusion solution to be filled into the storage space from an outside; and a ventilation port located at the inner wall and configured to allow gas in the storage space to be discharged to the outside.

7 Claims, 10 Drawing Sheets

(51) Int. Cl.
*A61J 1/20* (2006.01)
*A61M 5/36* (2006.01)
*A61M 5/38* (2006.01)
*A61J 1/14* (2023.01)

(52) U.S. Cl.
CPC .............. *A61M 5/36* (2013.01); *A61M 5/385* (2013.01); *A61J 1/145* (2015.05)

(58) Field of Classification Search
CPC ............ A61M 39/20; A61M 2205/123; A61M 2205/7536; A61M 5/36; A61M 5/385; A61J 1/05; A61J 1/16; A61J 1/10; A61J 1/2075; A61J 1/2082; A61J 1/145
See application file for complete search history.

(56) References Cited

U.S. PATENT DOCUMENTS

| | | | | |
|---|---|---|---|---|
| 5,656,032 A * | 8/1997 | Kriesel | ............... | A61M 5/1413 604/890.1 |
| 2013/0324928 A1* | 12/2013 | Kruse | ............... | A61M 5/16854 604/151 |
| 2020/0253823 A1* | 8/2020 | Wu | ..................... | A61M 5/1413 |

FOREIGN PATENT DOCUMENTS

| | | | | |
|---|---|---|---|---|
| JP | 2004-097247 A | 4/2004 | | |
| JP | 2014-500764 A | 1/2014 | | |
| JP | 2014-523313 A | 9/2014 | | |
| WO | WO-9503078 A1 * | 2/1995 | ............ | A61M 5/142 |

OTHER PUBLICATIONS

International Searching Authority, “Written Opinion,” issued in connection with International Patent Application No. PCT/JP2020/039253, dated Jan. 12, 2021.

International Searching Authority, “Written Opinion,” issued in connection with PCT Application No. PCT/JP2020/039253, dated Jan. 12, 2021, with English translation (8 pages).

* cited by examiner

INFUSION CARTRIDGE AND INFUSION PUMP

CROSS-REFERENCE TO RELATED APPLICATIONS

This is a bypass continuation of PCT Application No. PCT/JP2020/039253, filed on Oct. 19, 2020, which claims priority to Japanese Application No. 2019-215766, filed on Nov. 28, 2019, the contents of which are incorporated by reference in their entireties.

BACKGROUND

The present disclosure relates to an infusion cartridge and an infusion pump.

Conventionally, an infusion pump that imparts peristaltic movement to an infusion tube to feed an infusion solution such as a medicinal solution has been known. Japanese Patent Publication No. 2014-523313 A ("JP '313") describes an example of this type of infusion pump. JP'313 discloses a portable injection pump to which a cassette for storing a fluid storage bag is attached and which can feed an infusion solution in the fluid storage bag. A tube extends from the fluid storage bag described in JP'313, and an infusion solution is filled into the fluid storage bag from a syringe through the tube.

SUMMARY

When an infusion solution is filled into the fluid storage bag described in JP'313, air bubbles may accumulate in the fluid storage bag. Such air bubbles are likely to accumulate in a deformed part such as wrinkles generated in the fluid storage bag. The air bubbles that have accumulated are moved, for example, by striking the fluid storage bag to impart vibration, and collected in one place, or the posture of the liquid storage bag is changed to move large air bubbles and small air bubbles are collected, and then the air bubbles are discharged using a syringe. However, this work takes time and effort for a medical worker.

An object of the present disclosure is to provide an infusion cartridge that defines an infusion storage space in which air bubbles are less likely to accumulate and from which gas can be easily discharged, and an infusion pump.

An infusion cartridge as a first aspect of the present disclosure is an infusion cartridge that defines a storage space capable of storing an infusion solution, the infusion cartridge including: a case portion having a recess; and a film portion that has flexibility, covers an open side of the recess, and defines the storage space with the recess, in which on an inner wall that defines the storage space, a filling port capable of filling the infusion solution into the storage space from the outside, and a ventilation port capable of discharging gas in the storage space to the outside are formed.

As one embodiment of the present disclosure, the ventilation port is formed by a ventilation filter.

An infusion cartridge as one embodiment of the present disclosure includes a cover portion attached to the case portion and openable and closable with respect to the case portion between a state in which the cover portion does not cover the film portion and a state in which the cover portion covers the film portion.

As one embodiment of the present disclosure, the ventilation port is formed in the recess of the case portion.

As one embodiment of the present disclosure, the filling port is formed in the recess of the case portion.

As one embodiment of the present disclosure, a cylindrical portion protruding toward the storage space is formed on an inner surface of the recess, and the filling port is formed by a distal end opening of the cylindrical portion.

An infusion cartridge as one embodiment of the present disclosure includes a tube portion connected to the case portion so as to be able to fill the infusion solution through the filling port.

As one embodiment of the present disclosure, an outer surface of the case portion includes at least one planar portion, and the ventilation port is formed at a position farther from the planar portion than the filling port in an orthogonal direction orthogonal to the planar portion.

As one embodiment of the present disclosure, the ventilation port is formed on one end side of an inner wall that defines the storage space, the one end side being away from the planar portion in the orthogonal direction.

As one embodiment of the present disclosure, the film portion enters a bottom surface side from the open side of the recess in a state in which the infusion solution is not stored in the storage space.

An infusion pump as a second aspect of the present disclosure includes the infusion cartridge and a pump body to which the infusion cartridge is attachable.

The present disclosure can provide an infusion cartridge that defines an infusion storage space in which air bubbles are less likely to accumulate and from which gas can be easily discharged, and an infusion pump.

DETAILED DESCRIPTION

Figure 1:
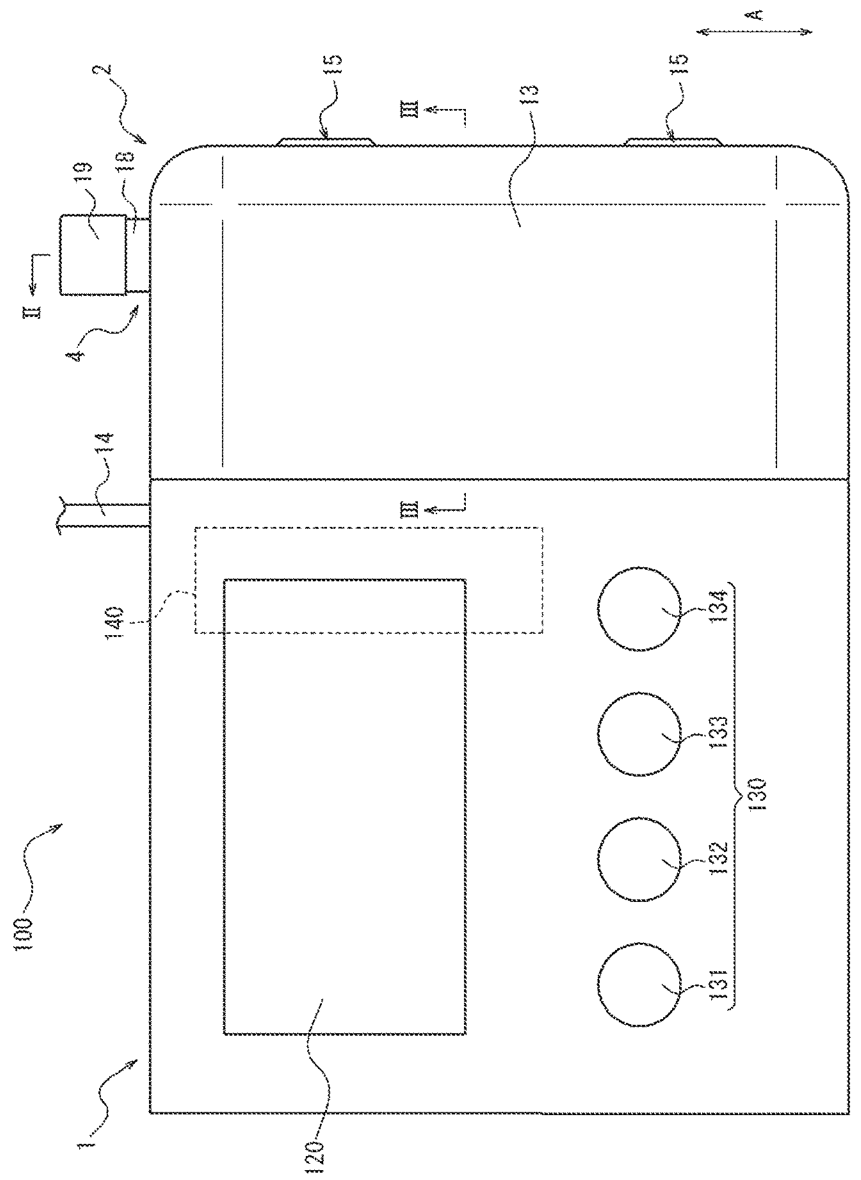
FIG. 1 is a front view illustrating an infusion pump as an embodiment of the present disclosure.

Hereinafter, an embodiment of an infusion cartridge and an infusion pump according to the present disclosure will be described by way of example with reference to the drawings. In the drawings, the same members and units are denoted by the same reference numeral.

FIG. 1 is a front view illustrating an infusion pump 100 as an embodiment of the infusion pump according to the present disclosure. As illustrated in FIG. 1, the infusion pump 100 includes a pump body 1 and an infusion cartridge 2 as an embodiment of the infusion cartridge according to the present disclosure. The infusion pump 100 illustrated in FIG. 1 can be used as, for example, a patient controlled analgesia (PCA) pump, but an application thereof is not particularly limited. In the infusion pump 100 of the present embodiment, the pump body 1 can be reused by replacing the disposable infusion cartridge 2.

<Pump Body 1>

As illustrated in FIG. 1, a display unit 120 on which various types of information are displayed and an operation unit 130 in which operation switches and the like are arranged are disposed on a front surface of the pump body 1. The display unit 120 displays, for example, a liquid feeding rate, an integrated dose, and the like. The display unit 120 may be a liquid crystal screen with a touch panel used for setting a liquid feeding rate and the like. The operation switches of the operation unit 130 illustrated in FIG. 1 are a fast delivery switch 131 that makes liquid feeding at a liquid feeding rate higher than a set liquid feeding rate (mL/h) possible while being pressed, a start switch 132 that starts liquid feeding by being pressed, a stop switch 133 that forcibly stops liquid feeding by being pressed, and a power supply switch 134 for instructing ON/OFF of power supply of the pump body 1. However, there may be other operation switches.

In addition, the pump body 1 includes a liquid feeding unit 140 that sandwiches a tube portion 14 of the infusion cartridge 2 between the pump body 1 and a tube receiving portion 30 of the infusion cartridge 2 to be attached and feeds an infusion in the tube portion 14 from a flow path upstream side to a flow path downstream side. The liquid feeding unit 140 of the present embodiment includes a plurality of fingers and a drive portion that drives the fingers. The plurality of fingers is disposed on a side surface of the pump body 1 facing the tube receiving portion 30 located on a side surface of the infusion cartridge 2. The plurality of fingers is arranged along an extending direction of the tube portion 14. Each of the fingers is driven by the drive portion so as to reciprocate in a direction facing the tube receiving portion 30 of the infusion cartridge 2. Each of the fingers moves so as to approach the infusion cartridge 2, and the tube portion 14 is thereby sandwiched between each of the fingers and the tube receiving portion 30. As a result, the tube portion 14 is occluded. The drive portion sequentially drives the fingers from a flow path upstream side toward a flow path downstream side in the extending direction of the tube portion 14. As a result, the tube portion 14 is sequentially occluded from the flow path upstream side toward the flow path downstream side, and peristaltically moves. Therefore, an infusion solution in the tube portion 14 can be fed from the flow path upstream side toward the flow path downstream side.

The pump body 1 is not limited to the configuration of the present embodiment. The pump body 1 may include a unit different from the above-described units, such as an air bubble detection sensor unit or a blockage sensor unit. In addition, as described above, in the liquid feeding unit 140 of the pump body 1 of the present embodiment, the tube portion 14 is pressed by the plurality of fingers, but a pressing portion different from the fingers may be used as long as the pressing portion can feed an infusion solution in the tube portion 14.

<Infusion Cartridge 2>

Figure 2:
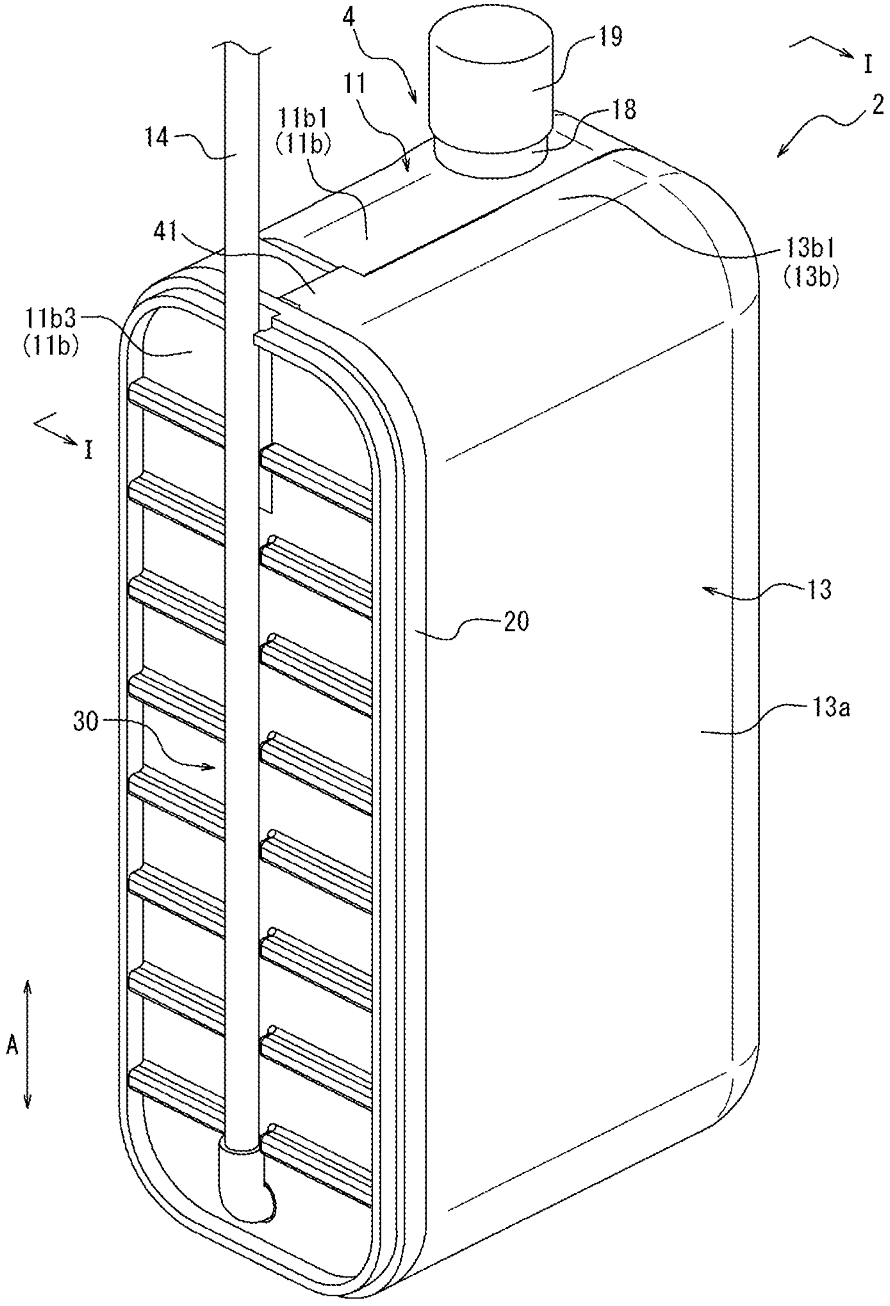
FIG. 2 is a perspective view of the single infusion cartridge illustrated in FIG. 1.
Figure 3:
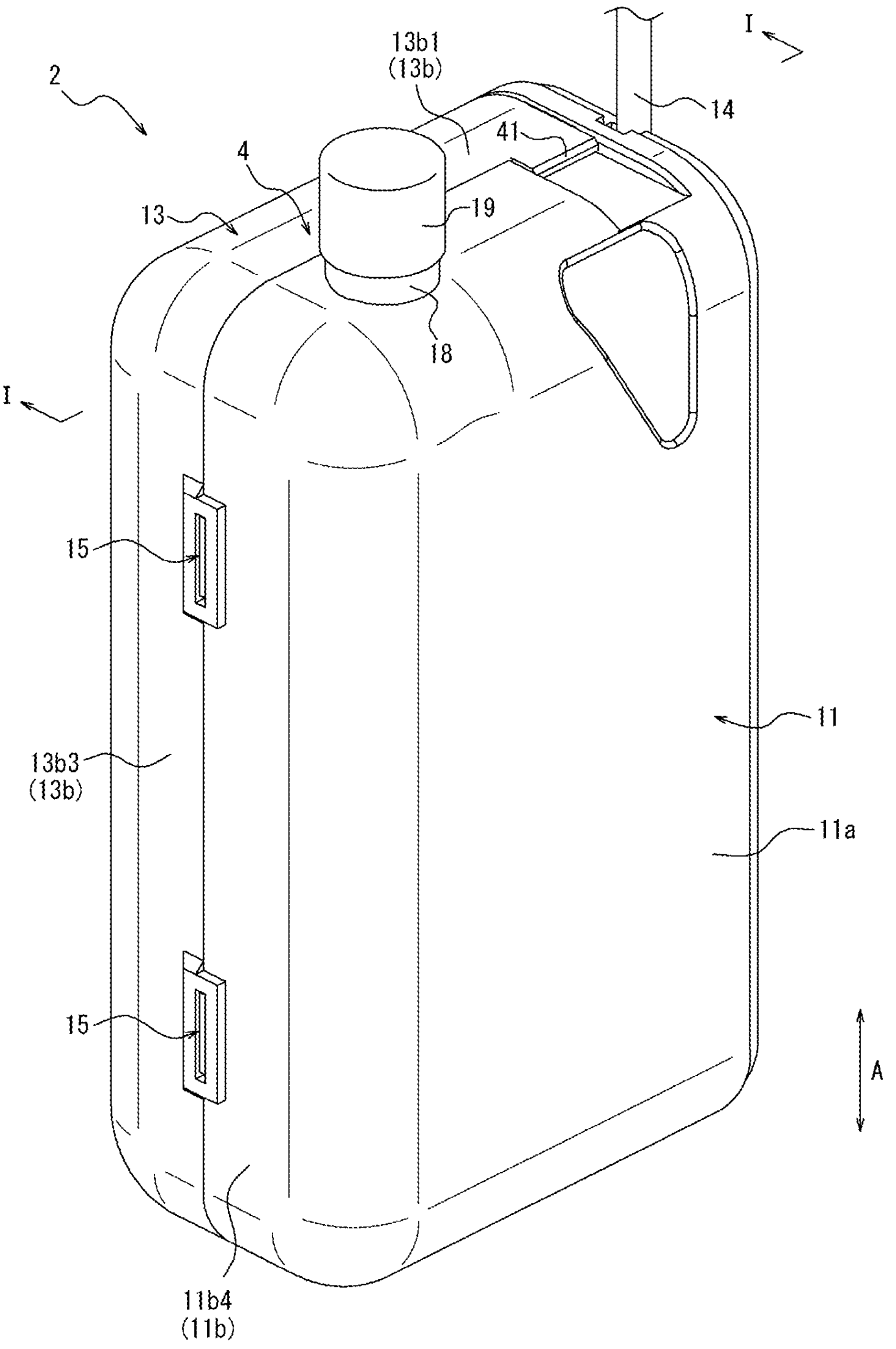
FIG. 3 is a perspective view of the single infusion cartridge illustrated in FIG. 1 as viewed from a viewpoint different from FIG. 2.
Figure 4:
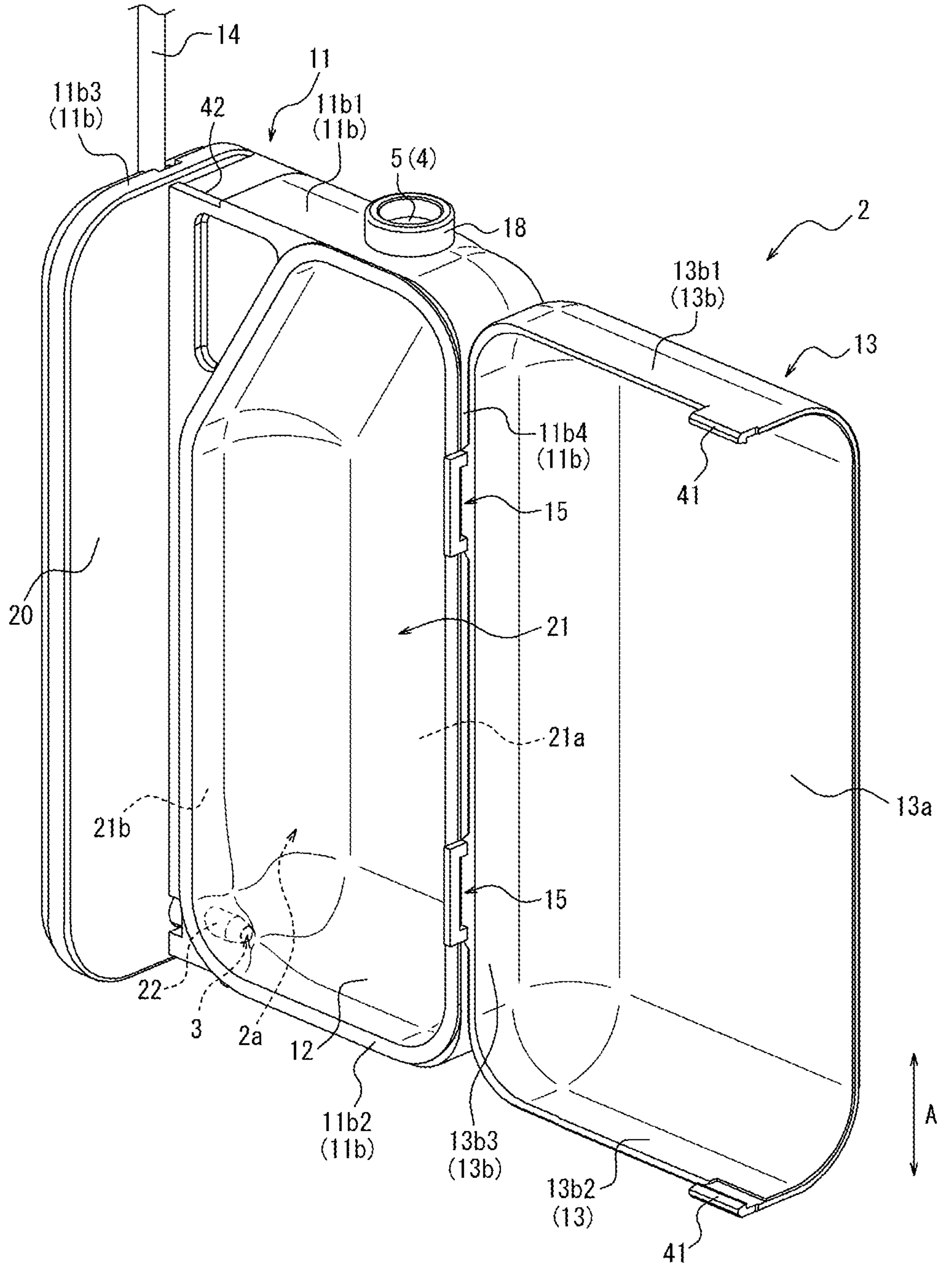
FIG. 4 is a perspective view illustrating a state in which the infusion cartridge illustrated in FIG. 2 is not filled with an infusion solution in a state in which a cover portion of the infusion cartridge is opened with respect to a case portion.
Figure 5:
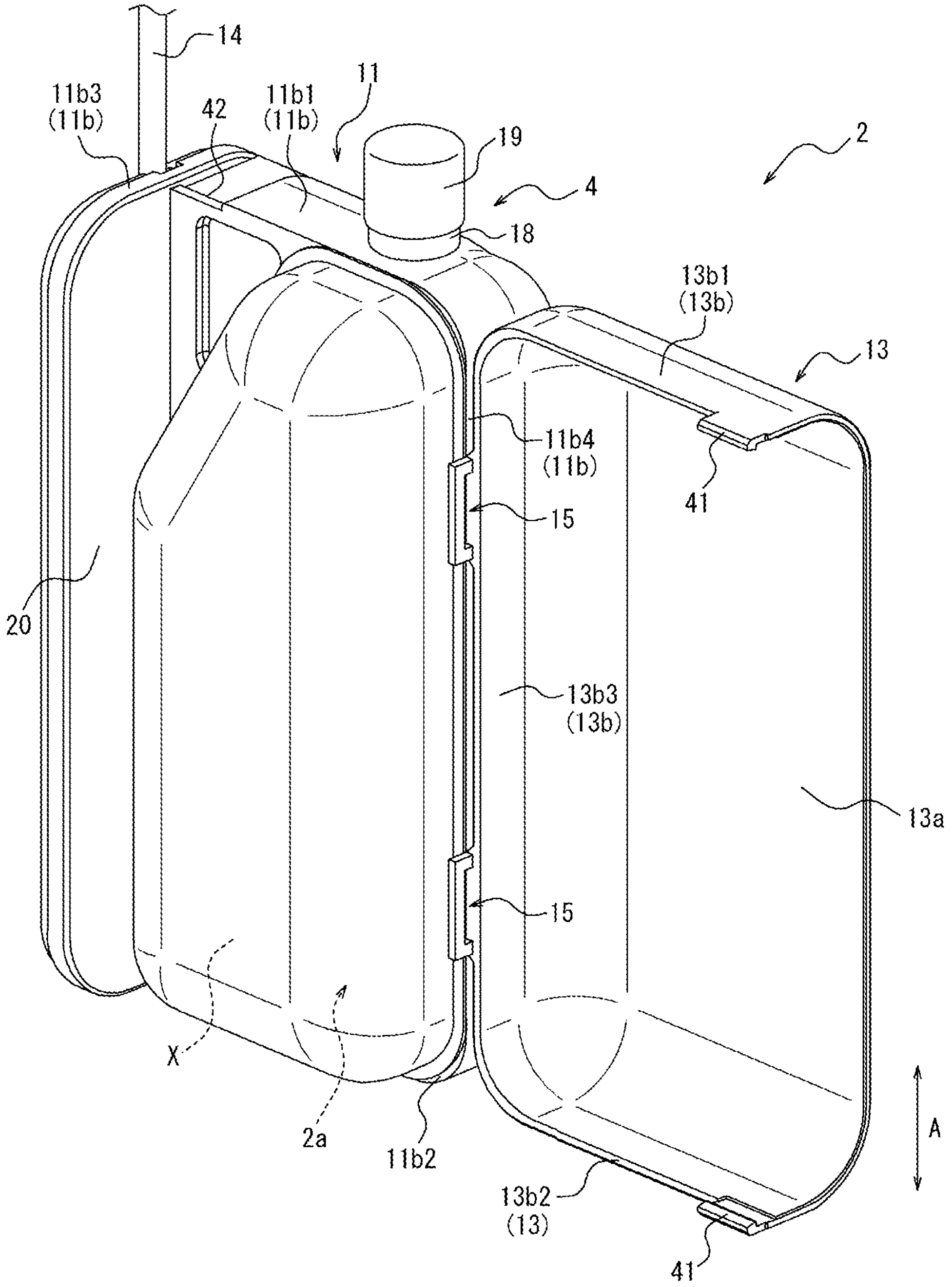
FIG. 5 is a perspective view illustrating a state in which the infusion cartridge illustrated in FIG. 2 is filled with an infusion solution in a state in which a cover portion of the infusion cartridge is opened with respect to a case portion.
Figure 6:
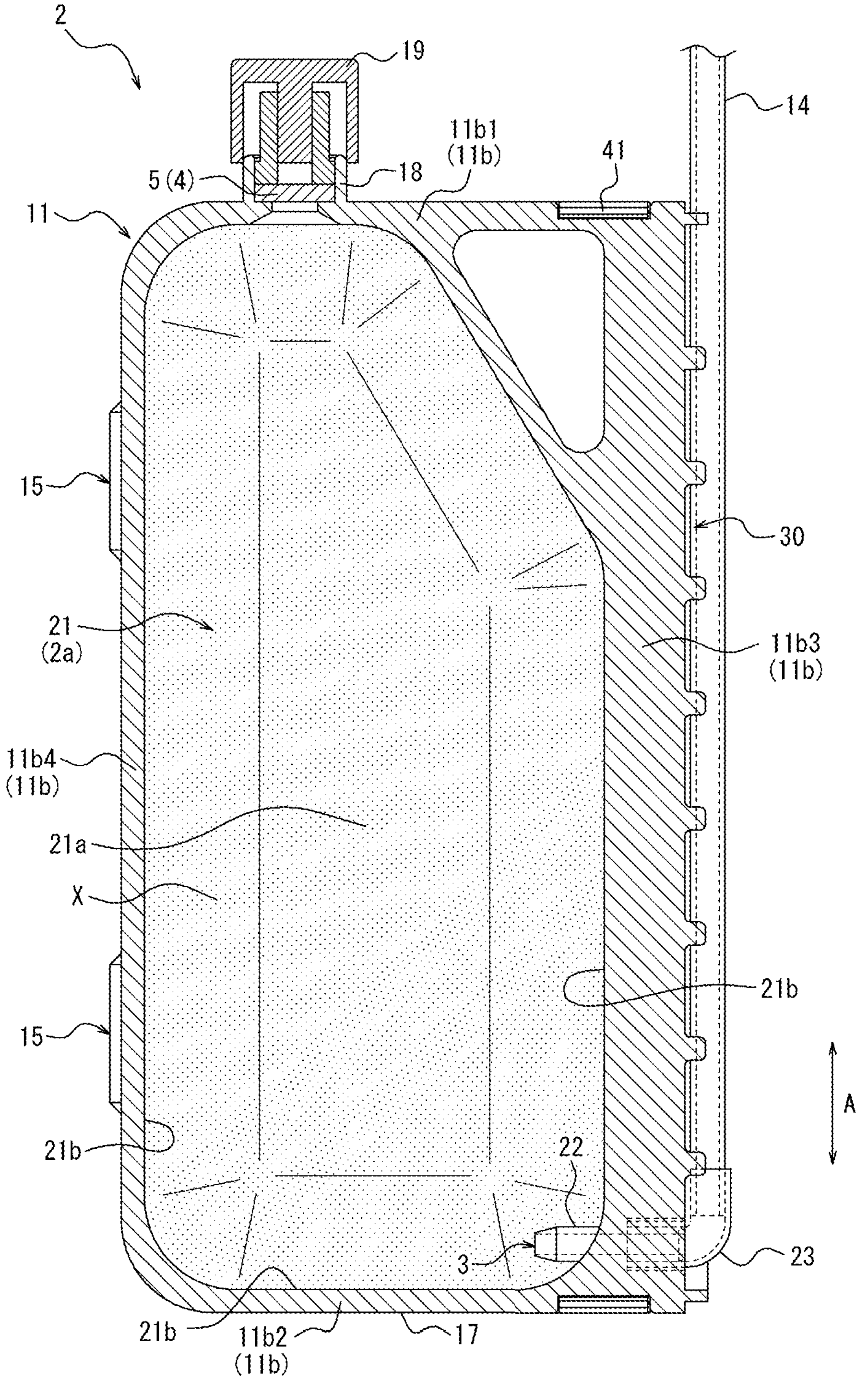
FIG. 6 is a cross-sectional view of the infusion cartridge in the state in which the infusion cartridge is filled with an infusion solution illustrated in FIG. 5.
Figure 7:
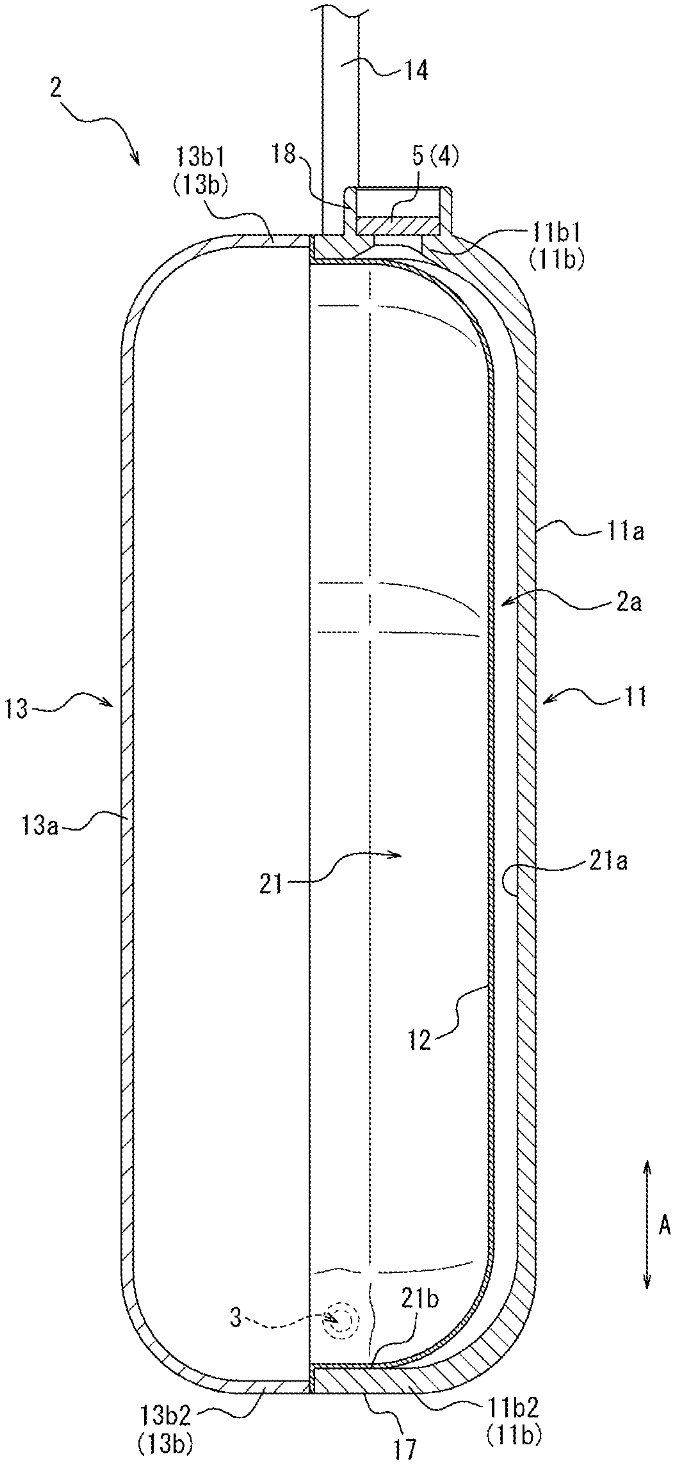
FIG. 7 is a cross-sectional view of the infusion cartridge in a state in which the storage space is not filled with an infusion solution.
Figure 8:
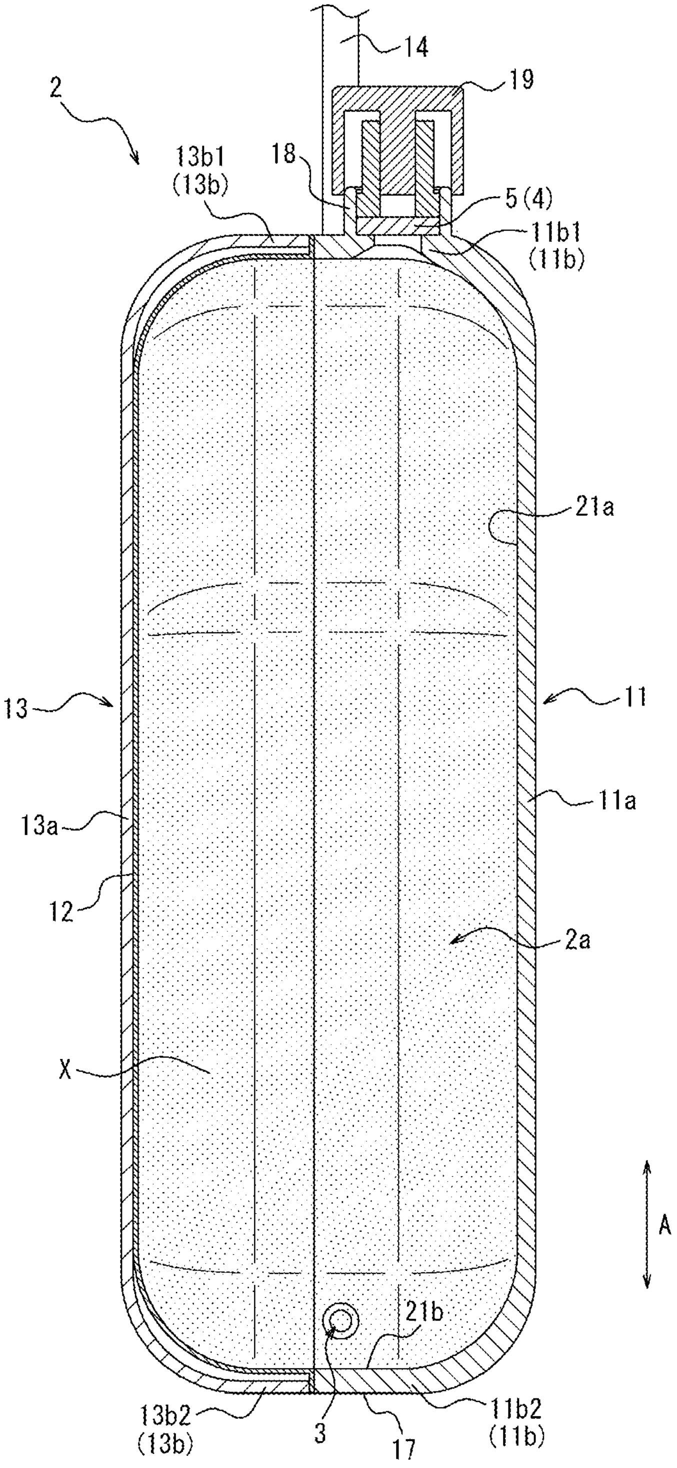
FIG. 8 is a cross-sectional view of the infusion cartridge at a position different from that of FIG. 7 in a state in which the storage space is filled with an infusion solution.
Figure 9:
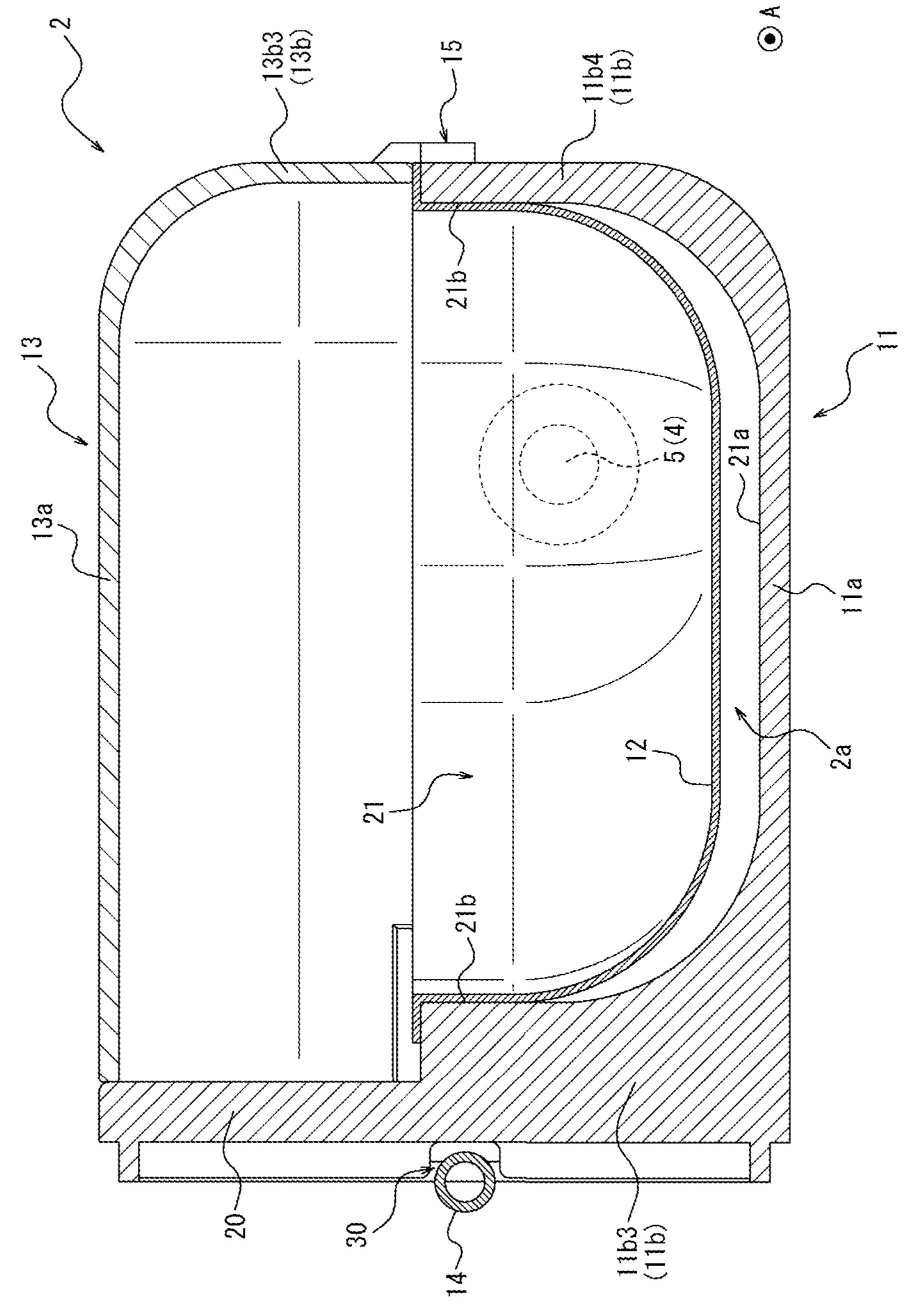
FIG. 9 is a cross-sectional view of the infusion cartridge at a position different from that of FIG. 6 in a state in which the storage space is not filled with an infusion solution.
Figure 10:
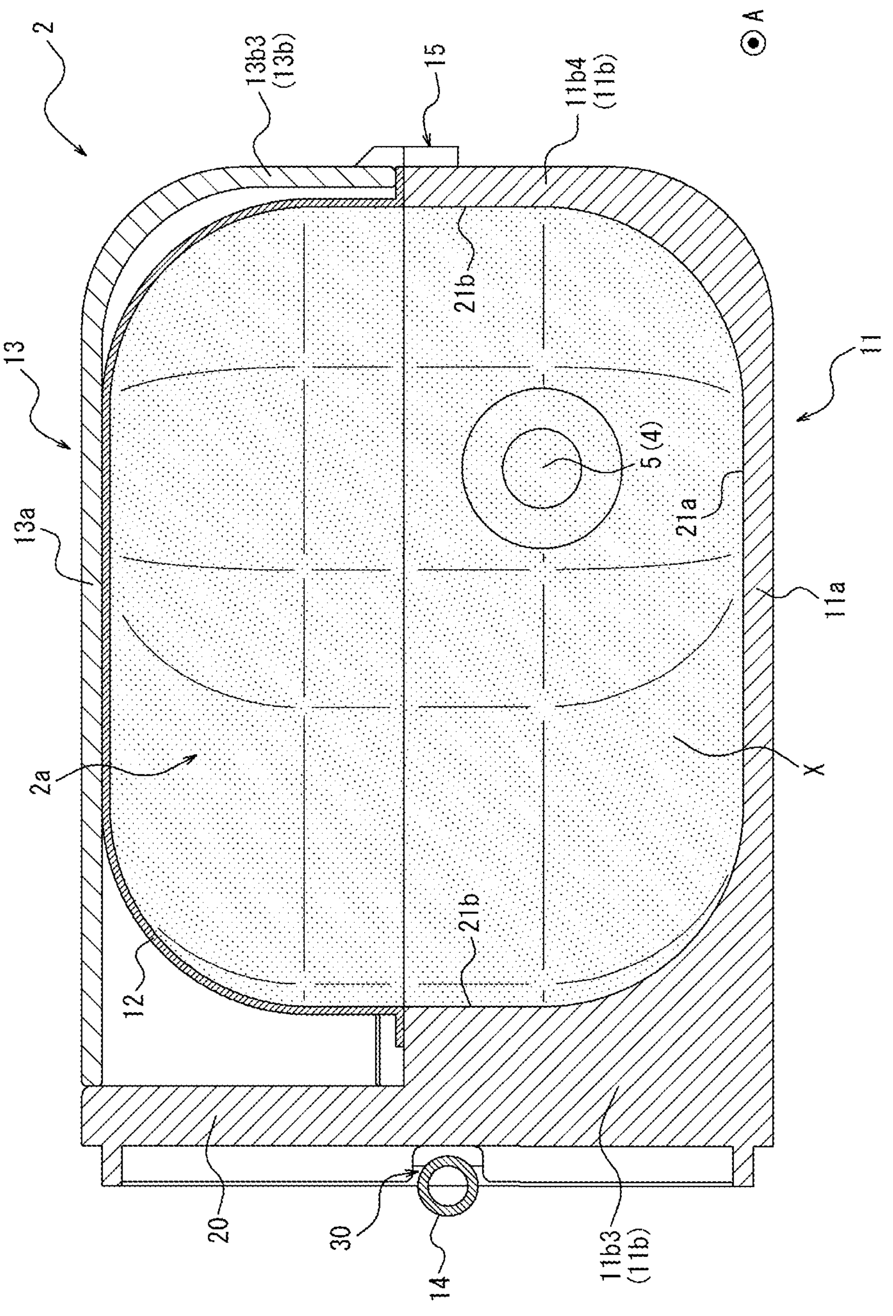
FIG. 10 is a cross-sectional view of the infusion cartridge at a position different from those of FIGS. 6 and 8 in a state in which the storage space is filled with an infusion solution.

FIGS. 2 and 3 are perspective views of the single infusion cartridge 2 as viewed from different viewpoints. FIGS. 4 and 5 are perspective views illustrating a state in which the cover portion 13 of the infusion cartridge 2 illustrated in FIGS. 2 and 3 is opened with respect to the case portion 11. FIG. 4 illustrates a state in which the infusion cartridge 2 is not filled with an infusion solution X. FIG. 5 illustrates a state in which the infusion cartridge 2 is filled with the infusion solution X. FIG. 6 is a cross-sectional view of the infusion cartridge 2 in a state in which the infusion cartridge 2 is filled with the infusion solution X illustrated in FIG. 5. The position of the cross section illustrated in FIG. 6 is the position of the cross section taken along line I-I illustrated in FIGS. 2 and 3. FIGS. 7 and 9 are cross-sectional views of the infusion cartridge 2 in a state in which a storage space 2*a* is not filled with the infusion solution X. FIGS. 8 and 10 are cross-sectional views of the infusion cartridge 2 in a state in which the storage space 2*a* is filled with the infusion solution X. FIGS. 7 and 8 are cross-sectional views taken along line II-II illustrated in FIG. 1. FIGS. 9 and 10 are cross-sectional views taken along line III-III illustrated in FIG. 1.

As illustrated in FIGS. 4 to 10, the infusion cartridge 2 defines the storage space 2*a* capable of storing the infusion solution X such as a medicinal solution. As illustrated in FIG. 4 and the like, the infusion cartridge 2 includes the case portion 11 and a film portion 12.

As illustrated in FIG. 4 and the like, a recess 21 is formed in the case portion 11. As illustrated in FIGS. 7 to 10, the recess 21 of the present embodiment includes a planar bottom surface 21*a* and a curved side surface 21*b* continuously rising from an outer edge of the bottom surface 21*a*. An open side of the recess 21 is formed by an end of the side surface 21*b* opposite to the bottom surface 21*a* side, that is, an edge of the recess 21. The recess 21 of the present embodiment has the above-described shape, but the shape of the recess 21 is not particularly limited. Therefore, the bottom surface 21*a* and the side surface 21*b* of the recess 21 may be planar or curved. However, the bottom surface 21*a* and the side surface 21*b* are preferably smoothly continuous with each other by a curved surface from a viewpoint of suppressing accumulation of air bubbles.

The film portion 12 has flexibility. As illustrated in FIGS. 4, 5, and 7 to 10, the film portion 12 covers an open side of the recess 21 of the case portion 11 and defines the storage space 2*a* with the recess 21. The film portion 12 of the present embodiment is joined to an edge of the recess 21. The case portion 11 and the film portion 12 can be joined to each other by, for example, welding, but a joining method is not particularly limited.

The case portion 11 has a formality that is not deformed even by an internal pressure of the infusion solution X stored in the storage space 2*a*. Examples of a material of the case portion 11 include various resin materials such as a polyolefin such as polyethylene, polypropylene, or an ethylene-propylene copolymer; an ethylene-vinyl acetate copolymer (EVA); polyvinyl chloride; polyvinylidene chloride; polystyrene; polyamide; polyimide; polyamideimide; polycarbonate; poly-(4-methylpentene-1); ionomer; an acrylic resin; polymethyl methacrylate; an acrylonitrile-butadiene-styrene copolymer (ABS resin); an acrylonitrile-styrene copolymer (AS resin); a butadiene-styrene copolymer; a polyester such as polyethylene terephthalate (PET), polybutylene terephthalate (PBT), or polycyclohexane terephthalate (PCT); polyether; polyetherketone (PEK); polyetheretherketone (PEEK); polyetherimide; polyacetal (POM); polyphenylene oxide; modified polyphenylene oxide; polysulfone; polyether sulfone; polyphenylene sulfide; polyarylate; aromatic polyester (liquid crystal polymer); polytetrafluoroethylene, polyvinylidene fluoride, and a fluorine-based resin. The case portion 11 is molded using, for example, any one of the above-described resin materials.

The film portion 12 is deformed by an internal pressure of the infusion solution X stored in the storage space 2*a*. The thickness of the film portion 12 is smaller than the thickness of the above-described case portion 11. The volume of the storage space 2*a* is changed by deformation of the film portion 12. Examples of a material of the film portion 12 include, in addition to the materials forming the case portion 11, various rubber materials such as a natural rubber, an isoprene rubber, a butadiene rubber, a styrene-butadiene rubber, a nitrile rubber, a chloroprene rubber, a butyl rubber, an acrylic rubber, an ethylene-propylene rubber, a hydrin rubber, a urethane rubber, a silicone rubber, and a fluororubber, and various thermoplastic elastomers such as a styrene-based elastomer, a polyolefin-based elastomer, a polyvinyl chloride-based elastomer, a polyurethane-based elastomer, a polyester-based elastomer, a polyamide-based elastomer, a polybutadiene-based elastomer, a transpolyisoprene-based elastomer, a fluororubber-based elastomer, and a chlorinated polyethylene-based elastomer, and a polyolefin such as polyethylene, polypropylene, or an ethylene-propylene copolymer is preferable. The film thickness of the film portion 12 can be, for example, 0.2 mm to 0.5 mm.

A filling port 3 and a ventilation port 4 are formed on an inner wall that defines the storage space 2*a*. The infusion solution X can be filled into the storage space 2*a* from the outside through the filling port 3. Gas in the storage space 2*a* can be discharged to the outside through the ventilation port 4.

As described above, the storage space 2*a* of the infusion cartridge 2 is defined by the recess 21 of the case portion 11 and the film portion 12 covering the recess 21. The filling port 3 and the ventilation port 4 are formed on an inner wall that defines the storage space 2*a*. With such a configuration, the inner wall of the recess 21 that defines the storage space 2*a* is not deformed by an internal pressure of the infusion solution X in the storage space 2*a*. As a result, deformation of the inner wall that defines the storage space 2*a* can be suppressed, and as a result, formation of wrinkles and the like in which air bubbles easily accumulate can be suppressed. Therefore, air bubbles are less likely to accumulate in the storage space 2*a*. In addition, by forming the ventilation port 4 separately from the filling port 3, gas in the storage space 2*a* can be discharged through the ventilation port 4 while the infusion solution X is filled from the filling port 3 into the storage space 2*a*. Therefore, gas can be easily discharged from the storage space 2*a* to the outside as compared with a configuration in which the ventilation port 4 is not formed in addition to the filling port 3.

In particular, the ventilation port 4 is preferably formed by a ventilation filter 5. Furthermore, as the ventilation filter 5, it is preferable to use a configuration in which a surface is hydrophobized or a hydrophobic film. Examples of a constituent material of the hydrophobic film include polytetrafluoroethylene (PTFE), a copolymer of tetrafluoroethylene and hexafluoropropylene (FEP), a copolymer of tetrafluoroethylene and perfluoroalkyl vinyl ether (PFA), and polyvinylidene fluoride (PVDF). The ventilation filter 5 preferably has a porous structure. The ventilation filter 5 having a porous structure can be obtained, for example, by making the above constituent material of the hydrophobic film porous by a method such as a stretching method, a micro phase separation method, an electron beam etching method, a sintering method, or argon plasma particles. A hydrophobizing method is not particularly limited, and for example, a method for coating a surface of the ventilation filter 5 with a hydrophobic constituent material may be used. Furthermore, the ventilation filter 5 is not limited to the above configuration as long as it has a hydrophobic configuration having a function of transmitting gas and not transmitting liquid, and may have a configuration including another material such as a hydrophilic material. With such a hydrophobic ventilation filter 5, gas in the storage space 2*a* can be discharged to the outside, and leaking of the infusion solution X in the storage space 2*a* to the outside can be suppressed.

Hereinafter, further details of the infusion cartridge 2 of the present embodiment will be described.

As illustrated in FIGS. 4, 5, and the like, the infusion cartridge 2 of the present embodiment includes the cover portion 13 and the tube portion 14 in addition to the case portion 11 and the film portion 12 described above. Hereinafter, further details of each portion of the infusion cartridge 2 of the present embodiment will be described.

The case portion 11 of the present embodiment includes a flat plate-shaped bottom plate portion 11*a* and a side plate portion 11*b* rising from an outer edge of the bottom plate portion 11*a* in a thickness direction of the bottom plate portion 11*a*. The bottom plate portion 11*a* has a substantially quadrangular outer shape in plan view as viewed in the thickness direction. The side plate portion 11*b* rises from four outer edges of the bottom plate portion 11*a* extending substantially linearly. The recess 21 of the case portion 11 of the present embodiment is defined by the bottom plate portion 11*a* and the side plate portion 11*b* described above. More specifically, the bottom surface 21*a* of the recess 21 of the present embodiment is formed by an inner surface of the bottom plate portion 11*a*. The side surface 21*b* of the recess 21 of the present embodiment is formed by an inner surface of the side plate portion 11*b*.

In the present embodiment, the filling port 3 is formed in the recess 21 of the case portion 11. Therefore, the position of the filling port 3 is not changed depending on presence or absence of the infusion solution X in the storage space 2*a* and the amount of the infusion solution X. Therefore, it is possible to enhance positional stability of the tube portion 14 described below, which is in fluid communication with the filling port 3.

In the present embodiment, the ventilation port 4 is formed in the recess 21 of the case portion 11. If the ventilation port 4 is formed in the film portion 12, the ventilation port 4 may be blocked by deformation of the film portion 12. On the other hand, by forming the ventilation port 4 in the recess 21 of the case portion 11, the ventilation port 4 is less likely to be blocked, and discharge of gas can be promoted.

Here, the side plate portion 11*b* of the case portion 11 of the present embodiment includes a first plate portion 11*b*1 having the ventilation port 4, a second plate portion 11*b*2 disposed so as to face the first plate portion 11*b*1, a third plate portion 11*b*3 continuous with one end of the first plate portion 11*b*1 and one end of the second plate portion 11*b*2, and a fourth plate portion 11*b*4 continuous with the other end of the first plate portion 11*b*1 and the other end of the second plate portion 11_b_2 and facing the third plate portion 11_b_3. The filling port 3 is formed in the third plate portion 11_b_3 of the side plate portion 11_b_.

The first plate portion 11_b_1 and the second plate portion 11_b_2 of the present embodiment each have a fastening portion 42 to be caught by a locking claw portion 41 of the cover portion 13 when the cover portion 13 described below is closed.

A part on an inner surface side of the third plate portion 11_b_3 of the present embodiment rises to the same height as top end surfaces of the first plate portion 11_b_1, the second plate portion 11_b_2, and the fourth plate portion 11_b_4. On the other hand, the remaining part on an outer surface side of the third plate portion 11_b_3 of the present embodiment further extends from the top end surfaces of the first plate portion 11_b_1, the second plate portion 11_b_2, and the fourth plate portion 11_b_4. Hereinafter, this extending part is referred to as an "extending portion 20". Therefore, the open side of the recess 21 of the present embodiment is formed by the top end surfaces of the first plate portion 11_b_1, the second plate portion 11_b_2, and the fourth plate portion 11_b_4, and the top end surface of a part on the inner surface side of the third plate portion 11_b_3.

The tube receiving portion 30 that receives the tube portion 14 and sandwiches the tube portion 14 with the pump body 1 is formed on an outer surface of the third plate portion 11_b_3. The tube receiving portion 30 of the present embodiment includes a groove into which the tube portion 14 is fitted.

The cover portion 13 described below is rotatably attached to the fourth plate portion 11_b_4 by a hinge portion 15.

A cylindrical portion 22 protruding toward the storage space 2_a_ is formed on an inner surface of the recess 21. The filling port 3 of the present embodiment is formed by a distal end opening of the cylindrical portion 22. More specifically, in the present embodiment, the cylindrical portion 22 is formed on an inner surface of the third plate portion 11_b_3. By forming the filling port 3 by the distal end opening of the cylindrical portion 22 in this manner, air bubbles adhering to an inner wall that defines the storage space 2_a_ are less likely to enter the filling port 3 as compared with a configuration without such a cylindrical portion 22. That is, even if there are air bubbles in the storage space 2_a_, it is difficult for the air bubbles to reach the distal end opening of the cylindrical portion 22, and discharge of the air bubbles from the filling port 3 can be suppressed.

As illustrated in FIG. 6, a proximal end side of the cylindrical portion 22 extends to an outside of the storage space 2_a_. The tube portion 14 described below is connected to the proximal end side of the cylindrical portion 22 via an L-shaped connection tube portion 23. As a result, a hollow portion of the tube portion 14 communicates with the storage space 2_a_ through the filling port 3. However, the connection configuration between the tube portion 14 and the filling port 3 is not limited to the configuration of the present embodiment.

An outer surface of the case portion 11 of the present embodiment includes five planar portions. Specifically, the case portion 11 of the present embodiment has one planar portion on each of an outer surface of the bottom plate portion 11_a_, an outer surface of the first plate portion 11_b_1, an outer surface of the second plate portion 11_b_2, an outer surface of the third plate portion 11_b_3, and an outer surface of the fourth plate portion 11_b_4. Here, for convenience of description, the planar portion of the outer surface of the second plate portion 11_b_2 is referred to as a "placement planar portion 17". In an orthogonal direction A orthogonal to the placement planar portion 17, the ventilation port 4 is formed at a position farther from the placement planar portion 17 than the filling port 3. Therefore, by placing the placement planar portion 17 on a horizontal plane, the ventilation port 4 can be located on an upper side in the vertical direction than the filling port 3. As a result, when the infusion solution X is filled into the storage space 2_a_ from the filling port 3, gas in the storage space 2_a_ is pushed upward in the vertical direction by the infusion solution X and discharged from the ventilation port 4. In addition, by filling the infusion solution X from the filling port 3 into the storage space 2_a_, gas in the storage space 2_a_ can be discharged through the ventilation port 4. In other words, it is only required to form at least one planar portion such as the above-described placement planar portion 17 on the outer surface of the case portion 11. As a result, gas in the storage space 2_a_ can be easily discharged.

In the present embodiment, by also placing a planar portion on an outer surface of the third plate portion 11_b_3 on a horizontal plane similarly to the planar portion on the outer surface of the above-described second plate portion 11_b_2, the ventilation port 4 can be located on an upper side in the vertical direction than the filling port 3. However, the tube receiving portion 30 that receives the tube portion 14 and sandwiches the tube portion 14 with the pump body 1 is formed on the outer surface of the third plate portion 11_b_3 as described above. Therefore, in the present embodiment, the above-described placement planar portion 17 is preferably disposed on the outer surface of the second plate portion 11_b_2 different from the third plate portion 11_b_3.

Furthermore, the ventilation port 4 of the present embodiment is formed on one end side (upper side in FIG. 6) of an inner wall that defines the storage space 2_a_, the one end side being away from the placement planar portion 17 in the orthogonal direction A. More specifically, the ventilation port 4 of the present embodiment is formed in the first plate portion 11_b_1 on one end side of an inner wall that defines the storage space 2_a_, the one end side being away from the placement planar portion 17 in the orthogonal direction A. Since the ventilation port 4 is on one end side (upper side in FIG. 6) in the orthogonal direction A, if the infusion solution X is filled from the filling port 3 into the storage space 2_a_ in a state in which the placement planar portion 17 is placed on a horizontal plane, the ventilation port 4 is less likely to be blocked with the infusion solution X that has been filled, and gas is likely to accumulate around the ventilation port 4. Therefore, gas can be continuously discharged from the ventilation port 4 until a large part of the storage space 2_a_ is filled with the infusion solution X. As a result, gas in the storage space 2_a_ can be more easily discharged to the outside.

The ventilation port 4 may be formed on one end side (upper side in FIG. 6) of an inner wall that defines the storage space 2_a_, the one end side being away from the placement planar portion 17 in the orthogonal direction A. The ventilation port 4 may be formed in the third plate portion 11_b_3, for example. In such a case, the ventilation port 4 is covered with the pump body 1 when the infusion cartridge 2 is attached to the pump body 1. Therefore, a cap member 19 described below to be attached to the ventilation port 4 does not need to have a fixed fitting structure.

The filling port 3 of the present embodiment is formed on the other end side (lower side in FIG. 6) of an inner wall that defines the storage space 2_a_, the other end side being close to the placement planar portion 17 in the orthogonal direction A. More specifically, the filling port 3 of the present embodiment is formed at an end of an inner surface of the third plate portion **11*b*3 on the second plate portion 11*b*2 side. The infusion pump 100 is usually used in a state in which the placement planar portion 17 is placed on a horizontal plane. When the infusion pump 100 is used, the infusion solution X that has been filled into the storage space 2*a* is administered into a living body from the filling port 3 through the tube portion 14. When the infusion pump 100 is used in this way, if the filling port 3 is on the other end side (lower side in FIG. 6) close to the placement planar portion 17, even if air bubbles remain in the storage space 2*a*, the air bubbles are less likely to be discharged from the filling port 3**. Therefore, enter of air bubbles into a living body can be suppressed.

Furthermore, as described above, the ventilation port 4 of the present embodiment is formed by the ventilation filter 5. More specifically, a cylindrical portion 18 protruding outward is formed on an outer surface of the first plate portion **11*b*1 of the side plate portion 11*b* of the case portion 11. The cylindrical portion 18 defines a communication hole that allows the outside and the storage space 2*a* to communicate with each other. The ventilation filter 5 is disposed in the communication hole. As illustrated in FIGS. 4, 5, 7, and 8, after the infusion solution X is filled into the storage space 2*a*, the cap member 19 is attached to the cylindrical portion 18. The cap member 19 can block the communication hole of the cylindrical portion 18. As a result, inflow of gas into the storage space 2*a* from the outside through the ventilation port 4 can be prevented. The configuration of the cap member 19 is not particularly limited as long as it can block the cylindrical portion 18 by being attached to the cylindrical portion 18. However, the cap member 19 preferably has a fixed fitting structure in which the cap member is not removable once attached to the cylindrical portion 18 such that there is no inflow of gas through the ventilation port 4 after the storage space 2*a* is once filled with the infusion solution X. However, as described above, the cap member 19 does not need to have a fixed fitting structure if the position of the ventilation port 4** is different.

The film portion 12 of the present embodiment can be deformed. As illustrated in FIGS. 7 and 8, the film portion 12 of the present embodiment enters the bottom surface **21*a* side from the open side of the recess 21 in a state in which the infusion solution X is not stored in the storage space 2*a*. In other words, the film portion 12 of the present embodiment is recessed along an inner surface of the recess 21 in a state in which the infusion solution X is not stored in the storage space 2*a*. As illustrated in FIGS. 9 and 10, when the infusion solution X is filled into the storage space 2*a*, the film portion 12 is pressed by the infusion solution X that has been filled and swells, and is deformed so as to protrude from the open side of the recess 21 and bulges. When air bubbles remain in the infusion solution X that has been filled, the air bubbles can be discharged from the ventilation port 4 by blocking the other end side of the tube portion 14 described below and then pushing the bulging film portion 12 from the outside. In a case where the infusion solution X stored in the storage space 2*a* is administered into a living body from the filling port 3 through the tube portion 14 described below, when the amount of the infusion solution X in the storage space 2*a* decreases, the film portion 12 returns from the state illustrated in FIGS. 9 and 10 to the state illustrated in FIGS. 7 and 8 by the weight of the infusion solution X or a restoring force of the film portion 12 itself. That is, the film portion 12 entering the bottom surface 21*a* side from the open side of the recess 21 in a state in which the infusion solution X is not stored in the storage space 2*a* is formed. As a result, the volume of the storage space 2*a* can be reduced as the amount of the infusion solution X that has been filled into the storage space 2*a* is reduced. As a result, a large part of the infusion solution X stored in the storage space 2*a* can be easily fed through the filling port 3**.

The film portion 12 enters the bottom surface **21*a* side from the open side of the recess 21 in a state in which the infusion solution X is not stored in the storage space 2*a*, but is not in contact with the bottom surface 21*a*. This can suppress adhering and sticking of the film portion 12 and the bottom surface 21*a*** to each other. Therefore, an increase in filling resistance can be suppressed.

As illustrated in FIGS. 1 to 10, the cover portion 13 is attached to the case portion 11. The cover portion 13 can be opened and closed with respect to the case portion 11 between a state in which the cover portion 13 does not cover the film portion 12 and a state in which the cover portion 13 covers the film portion 12. Hereinafter, for convenience of description, a state in which the cover portion 13 does not cover the film portion 12 is simply referred to as an "opened state". A state in which the cover portion 13 covers the film portion 12 is simply referred to as a "closed state".

The cover portion 13 is in an opened state when the infusion solution X is filled into the storage space **2*a*. Therefore, when the infusion solution X is filled into the storage space 2*a*, even if air bubbles enter the storage space 2*a*, the storage space 2*a* can be easily deformed by pushing the film portion 12 from the outside. Therefore, as compared with a configuration in which the storage space 2*a* is completely surrounded by a hard member such as the case portion 11, air bubbles in the storage space 2*a* can be easily moved when the infusion solution X is filled into the storage space 2*a***.

Furthermore, the storage space **2*a* of the present embodiment is formed by covering an open side of the recess 21 of the case portion 11 with the film portion 12. Therefore, deformation of an inner wall of the storage space 2*a* can be limited only to a part formed by the film portion 12 as compared with a case where an inner wall that defines the storage space 2*a* is formed only by a flexible bag body. That is, a deformation aspect of the inner wall of the storage space 2*a* can be controlled to a desired aspect. As a result, it is possible to suppress local large deformation at an unintended position of the storage space 2*a* due to a pushing force applied in order to move air bubbles, and accumulation of the air bubbles. That is, air bubbles in the storage space 2*a*** can be moved more easily.

After the infusion solution X is filled into the storage space **2*a*, by setting the cover portion 13 to the closed state, it is possible to suppress a patient using the infusion pump 100 from taking out the infusion solution X such as a medicinal solution in the storage space 2*a***.

The cover portion 13 of the present embodiment is rotatably attached to the case portion 11 by the hinge portion 15. Therefore, the state of the cover portion 13 can be changed between the opened state and the closed state described above by being rotated with respect to the case portion 11 by the hinge portion 15.

More specifically, the cover portion 13 of the present embodiment includes a top plate portion **13*a* that covers the film portion 12 in the closed state, and a side plate portion 13*b* that rises in a thickness direction of the top plate portion 13*a* from an outer edge of the top plate portion 13*a*. The top plate portion 13*a* faces the bottom plate portion 11*a* of the case portion 11 in the closed state of the cover portion 13. Therefore, the film portion 12 is interposed between the bottom plate portion 11***a* of the case portion 11 and the top plate portion 13*a* of the cover portion 13 in the closed state of the cover portion 13. In the closed state of the cover portion 13, the side plate portion 13*b* of the cover portion 13 covers a periphery of the storage space 2*a* in a direction orthogonal to the thickness direction of the bottom plate portion 11*a* and the top plate portion 13*a* together with the side plate portion 11*b* of the case portion 11. That is, by setting the cover portion 13 to the closed state, the storage space 2*a* is surrounded by the case portion 11 and the cover portion 13.

More specifically, the side plate portion 13*b* of the cover portion 13 of the present embodiment includes a first plate portion 13*b*1 in contact with the first plate portion 11*b*1 of the case portion 11, a second plate portion 13*b*2 in contact with the second plate portion 11*b*2 of the case portion 11, and a third plate portion 13*b*3 in contact with the fourth plate portion 11*b*4 of the case portion 11. The first plate portion 13*b*1 and the second plate portion 13*b*2 of the cover portion 13 have locking claw portions 41 to be caught by the fastening portions 42 of the first plate portion 11*b*1 and the second plate portion 11*b*2 of the case portion 11 in the closed state of the cover portion 13, respectively. The third plate portion 13*b*3 of the cover portion 13 is attached to the fourth plate portion 11*b*4 of the case portion 11 by the hinge portion 15.

The second plate portion 13*b*2 of the side plate portion 13*b* of the cover portion 13 does not protrude outward in the orthogonal direction A from the second plate portion 11*b*2 of the side plate portion 11*b* of the case portion 11 regardless of the opened/closed state of the cover portion 13. Therefore, the infusion cartridge 2 is self-standing on a horizontal plane by the placement planar portion 17 on an outer surface of the second plate portion 11*b*2 of the case portion 11 regardless of the opened/closed state of the cover portion 13. As a result, in the infusion cartridge 2 of the present embodiment, the infusion solution X can be easily filled into the storage space 2*a* in a state in which the placement planar portion 17 is placed on a horizontal plane. More specifically, in the closed state, an outer surface of the second plate portion 13*b*2 of the side plate portion 13*b* of the cover portion 13 of the present embodiment is substantially flush with the placement planar portion 17 of an outer surface of the second plate portion 11*b*2 of the side plate portion 11*b* of the case portion 11. The above-described fastening portion 42 of the case portion 11 is formed in a recess recessed inward from the placement planar portion 17 of the second plate portion 11*b*2. The locking claw portion 41 of the second plate portion 13*b*2 of the cover portion 13 is caught by the fastening portion 42 in a state of entering the above-described recess of the second plate portion 11*b*2 of the case portion 11 in the closed state of the cover portion 13. Therefore, in the present embodiment, the fastening portion 42 of the second plate portion 11*b*2 of the case portion 11 and the locking claw portion 41 of the second plate portion 13*b*2 of the cover portion 13 do not protrude to the outside of the placement planar portion 17 regardless of the opened/closed state of the cover portion 13.

The cover portion 13 of the present embodiment can be formed of a similar material to that of the above-described case portion 11. The thickness of the cover portion 13 is also larger than the thickness of the film portion 12.

The tube portion 14 is connected to the case portion 11 such that the infusion solution X can be filled through the filling port 3. As described above, one end side of the tube portion 14 of the present embodiment is connected to a proximal end side of the cylindrical portion 22 via the L-shaped connection tube portion 23. By connecting, for example, a syringe to the other end side of the tube portion 14, the infusion solution X can be filled into the storage space 2*a* through the tube portion 14.

When the infusion pump 100 is used, the tube portion 14 is used as a part of an infusion tube that administers the infusion solution X that has been filled into the storage space 2*a* into a living body. That is, the infusion pump 100 illustrated in FIG. 1 can feed the infusion solution X discharged from the storage space 2*a* to the tube portion 14 through the filling port 3 to a flow path downstream side by causing peristaltic movement in the tube portion 14. On the flow path downstream side of the tube portion 14, for example, there is an indwelling needle indwelled in a living body, and the infusion solution X can be administered into the living body through the indwelling needle.

The infusion cartridge and the infusion pump according to the present disclosure are not limited to the specific configurations illustrated in the above-described embodiment, and various modifications and changes can be made without departing from the scope of claims. Therefore, for example, the shape of the infusion cartridge 2 is not limited to the shape illustrated in the above-described embodiment, and can be appropriately designed according to the shape of the pump body 1 or the like. Specifically, in the above-described embodiment, the bottom plate portion 11*a* and the side plate portion 11*b* of the case portion 11 are connected to each other by a curved surface, but may be connected to each other by a corner portion. In the cover portion 13, the top plate portion 13*a* and the side plate portion 13*b* are connected to each other by a curved surface, but may be connected to each other by a corner portion.

REFERENCE CHARACTER LIST

1 Pump body
2 Infusion cartridge
2*a* Storage space
3 Filling port
4 Ventilation port
5 Ventilation filter
11 Case portion
11*a* Bottom plate portion
11*b* Side wall portion
11*b*1 First plate portion
11*b*2 Second plate portion
11*b*3 Third plate portion
11*b*4 Fourth plate portion
12 Film portion
13 Cover portion
13*a* Top plate portion
13*b* Side plate portion
13*b*1 First plate portion
13*b*2 Second plate portion
13*b*3 Third plate portion
14 Tube portion
15 Hinge portion
17 Placement planar portion (planar portion)
18 Cylindrical portion
19 Cap member
20 Extending portion
21 Recess
21*a* Bottom surface
21*b* Side surface
22 Cylindrical portion
23 Connection tube portion
41 Locking claw portion

42 Fastening portion
100 Infusion pump
120 Display unit
130 Operation unit
131 Fast delivery switch
132 Start switch
133 Stop switch
134 Power supply switch
140 Liquid feeding unit
A Orthogonal direction
X Infusion

The invention claimed is:

1. An infusion cartridge comprising:
a case portion comprising:
a flat plate-shaped bottom plate portion, and
a side plate portion rising from an outer edge of the bottom plate portion in a thickness direction of the bottom plate portion, wherein:
the flat plate-shaped bottom plate portion and the side plate portion together define a recess, and
the side plate portion comprises:
a first plate portion,
a second plate portion that faces the first plate portion,
a third plate portion that is continuous with a first end of the first plate portion and a first end of the second plate portion, and
a fourth plate portion that is continuous with a second end of the first plate portion and a second end of the second plate portion that faces the third plate portion; and
a film portion that has flexibility and covers an open side of the recess; wherein:
the flat plate-shaped bottom plate portion, and side plate portion, and the film portion together define a storage space configured to store an infusion solution;
the infusion cartridge further comprises:
a cylindrical portion protruding from an inner surface of the third plate portion into the storage space, wherein a filling port is located at a distal end opening of the cylindrical portion, the filling port being configured to allow the infusion solution to be filled into the storage space from an outside; and
a ventilation port located at the first plate portion and configured to allow gas in the storage space to be discharged to the outside.

2. The infusion cartridge according to claim 1, wherein the ventilation port comprises a ventilation filter.

3. The infusion cartridge according to claim 1, comprising a cover portion attached to the case portion and openable and closable with respect to the case portion between a state in which the cover portion does not cover the film portion and a state in which the cover portion covers the film portion.

4. The infusion cartridge according to claim 1, further comprising a tube portion connected to the case portion and configured to allow the infusion solution to be filled into the storage space via the filling port.

5. The infusion cartridge according to claim 1, wherein:
an outer surface of the second plate portion comprises a planar portion; and
a distance from the planar portion to the ventilation port is greater than a distance from the planar portion to the filling port in a direction orthogonal to the planar portion.

6. The infusion cartridge according to claim 1, wherein, in a state in which the infusion solution is not stored in the storage space, the film portion is located in the recess at a surface of the case portion that is opposite the open side of the recess.

7. An infusion pump comprising:
an infusion cartridge comprising:
a case portion comprising:
a flat plate-shaped bottom plate portion, and
a side plate portion rising from an outer edge of the bottom plate portion in a thickness direction of the bottom plate portion, wherein:
the flat plate-shaped bottom plate portion and the side plate portion together define a recess, and
the side plate portion comprises:
a first plate portion,
a second plate portion that faces the first plate portion,
a third plate portion that is continuous with a first end of the first plate portion and a first end of the second plate portion, and
a fourth plate portion that is continuous with a second end of the first plate portion and a second end of the second plate portion that faces the third plate portion, and
a film portion that has flexibility and covers an open side of the recess, wherein:
the flat plate-shaped bottom plate portion, and side plate portion, and the film portion together define a storage space configured to store an infusion solution, and
the infusion cartridge further comprises:
a cylindrical portion protruding from an inner surface of the third plate portion into the storage space, wherein a filling port is located at a distal end opening of the cylindrical portion, the filling port being configured to allow the infusion solution to be filled into the storage space from an outside, and
a ventilation port located at the first plate portion and configured to allow gas in the storage space to be discharged to the outside; and
a pump body to which the infusion cartridge is attachable.

* * * * *